United States Patent [19]
Titmas

[11] Patent Number: 5,563,073
[45] Date of Patent: Oct. 8, 1996

[54] PERSONAL BLOOD ALCOHOL LEVEL TESTING KIT

[76] Inventor: Ted Titmas, 16743 Oakview Dr., Encino, Calif. 91436

[21] Appl. No.: 436,925

[22] Filed: May 8, 1995

Related U.S. Application Data

[63] Continuation of Ser. No. 114,610, Aug. 31, 1993, abandoned.

[51] Int. Cl.$^6$ .............................. C12Q 1/28; C12Q 1/26
[52] U.S. Cl. .................. 436/132; 422/56; 422/61; 435/25; 435/28; 435/805
[58] Field of Search ......................... 436/132, 900; 422/58, 61, 56; 435/25, 26, 28, 805

[56] References Cited

U.S. PATENT DOCUMENTS 1,967,557  7/1934  John ........................................ 422/61
4,786,596  11/1988  Adams .................................... 436/132

Primary Examiner—Lyle A. Alexander
Attorney, Agent, or Firm—Poms, Smith, Lande & Rose

[57] ABSTRACT

A personal blood alcohol level testing kit utilizing alcohol-sensitive pads which are stored in a package that permits the storage of the alcohol-sensitive pads within its interior without exposing the alcohol-sensitive pads to ultraviolet light, moisture or air. The kit comprises at least one pad being chemically sensitive to alcohol. The alcohol-sensitive pads are stored in a package that is preferably formed from aluminum foil and paper. The personal blood alcohol level testing kit stores the alcohol-sensitive pads without exposing them to ultraviolet light, moisture or air, is portable, is inexpensive, may contain more than one blood alcohol level test, is easy to administer, is accurate and is self-contained.

18 Claims, 1 Drawing Sheet

PERSONAL BLOOD ALCOHOL LEVEL TESTING KIT

This is a continuation of application Ser. No. 08/114,610 filed on Aug. 31, 1993 now abandoned.

FIELD OF THE INVENTION

The present invention relates in general to personal blood alcohol level testing kits and more particularly to the packaging for storing the alcohol-sensitive pads of a personal blood alcohol level testing kit and to the method for testing the blood alcohol level of a user. The invention is applicable to the storage of the alcohol-sensitive pads which must be protected from any contact with ultraviolet light, moisture, or air.

BACKGROUND OF THE INVENTION

The public has become increasingly aware of the risks of drunk driving. As drunk driving accidents have increased, the penalties imposed on drunk drivers have become more severe. Unfortunately, it is very difficult for a drinker or their passengers or friends to know when their blood alcohol level is at a too high level for them to drive. Typically, there are no readily available means for the public to test the level of alcohol in a drinker's blood to determine whether they should not be driving.

Any blood alcohol testing kit must have a number of features to be practical. First, it must be portable, so that it may be discreetly carried in a wallet, pocket or purse because its use will be mainly at social events. The testing kit also must be inexpensive so that individual drinkers will be apt to purchase the kit. Further, if the testing kit is inexpensive, owners of establishments where alcohol is served or companies that manufacture and/or sell the alcohol will be apt to purchase the testing kits so that they may provide customers with blood alcohol level testing kits as a public service. The personal blood alcohol level testing kit must also contain more than one test so that the test may be performed more than once in an evening to thereby measure blood alcohol levels over time to determine when it is again safe for the user to drive. Further, if more than one person will be travelling in the car, then each person can test their blood alcohol level to determine which one has a blood alcohol level below the limit where they should not be driving so that the most sober of the group can be the designated driver. The kit must also be self-contained, that is, all the necessary items, including instructions and any charts or graphs, should be included within or on the packaging. The blood alcohol level test kit must also be easy to administer-easy enough so that even after a few drinks, the user can perform the test. The test must also be accurate and reproducible and useable without the taking of the user's blood.

It is well-known that a person's saliva contains the same concentration of alcohol as found in that person's blood. One known method for determining the level of blood alcohol takes advantage of this fact by testing a person's saliva to determine blood alcohol levels. This method uses alcohol-sensitive pads that are formed from paper saturated with alcohol oxidase enzyme, alcohol peroxidase enzyme, dyes and a buffer. When these alcohol-sensitive pads are saturated with a person's saliva, they will change color according to the level of alcohol in that saliva. This change in color can be measured so that a certain, known color change, indicates a certain alcohol level. It has been found that measuring alcohol levels by this method, through the user's saliva, is approximately 98% accurate. This level of accuracy is much greater than the approximately 72% accuracy of measuring alcohol levels by a person's breath, as in a Breathalyzer™.

The above desired features for a personal blood alcohol level testing kit are met by a package containing an alcohol-sensitive pad. The alcohol-sensitive pads provide an accurate and reproducible means for measuring blood alcohol levels. They may also be cut into small pieces so that they may be portable and may be discreetly carried in a wallet, pocket or a purse. Further, because of their small size, more than one alcohol-sensitive pad may be packaged together so that more than one test may be provided in a single kit. The test using the alcohol-sensitive pads is easy to administer, only requiring the user to saturate the pad with their saliva, to wait a short period of time and to compare and match the color of the pad with the corresponding color to determine the blood alcohol level.

With all of its advantages, however, the alcohol-sensitive pads do have one significant drawback—they cannot be exposed to ultraviolet light, moisture, or air while being stored. Once they are exposed to either of these, the enzyme will deteriorate in approximately six hours and thus be useless to measure blood alcohol. By developing a package in which the alcohol-sensitive pads are stored while being protected from ultraviolet light, moisture, and air, a personal blood alcohol level testing kit could be developed having all of the above-described desired features.

Accordingly, a principal object of the present invention is to provide a personal blood alcohol level testing kit utilizing an alcohol-sensitive pad that is portable so that it may be discreetly carried in a wallet, pocket or purse, is inexpensive, preferably contains more than one test so that the test may be performed more than once or by more than one person in an evening, is easy to administer, is accurate, and does not require any of the user's blood.

A further object of the present invention is to provide a personal blood alcohol level testing kit that utilizes an alcohol-sensitive pad that is stored in a package that is inexpensive, portable and that can store at least one alcohol-sensitive pad without exposing the alcohol-sensitive pads to ultraviolet light, moisture or air.

It is yet another object of the present invention to provide a self-contained, personal blood alcohol level testing kit that utilizes an alcohol-sensitive pad that has printed on its exterior the instructions for administering the test and the range of colors of the alcohol-sensitive pads and their corresponding blood alcohol levels.

SUMMARY OF THE INVENTION

In accordance with the present invention, a package for storing the alcohol-sensitive pads of a personal blood level testing kit is provided which is portable so that it may be discreetly carried in a wallet, pocket or purse, is inexpensive, is self-contained and is capable of storing the alcohol-sensitive pads without exposing them to ultraviolet light, moisture, or air.

The foregoing objectives are achieved through a pad being chemically sensitive to alcohol. The pad is preferably impregnated with at least one alcohol-sensitive enzyme, at least one dye and at least one buffer. The pad changes its color when it is contacted with the user's saliva containing alcohol, the pad changing to a different color depending on the alcohol level of the user's saliva. These alcohol-sensitive pads are stored in a package, the package preferably being formed from aluminum foil and paper. The package preferably includes a first side wall comprised of a plurality of layers coupled together with at least one of the layers being formed from aluminum foil and a second side wall also comprised of a plurality of layers coupled together with at least one of the layers being formed from aluminum foil. The package is formed by coupling together the outer edge of the first side wall with the outer edge of the second side wall to form an interior for storing at least one alcohol-sensitive pad.

In one preferred embodiment of a package for storing the alcohol-sensitive pads of a personal blood alcohol testing kit, a first side wall having an inner and outer layer and a second side wall also having an inner and outer layer are provided. The inner layer of the first side wall and the inner layer of the second side wall are preferably formed from high-grade surgical aluminum foil. The outer layer of the first side wall and the outer layer of the second side wall are preferably formed from paper.

The first side wall is formed by coupling together the lower surface of the outer layer of the first side wall with the upper surface of the inner layer of the first side wall. The second side wall is formed by coupling together the lower surface of the inner layer of the second side wall with the upper surface of the outer layer of the second side wall. The package is then preferably formed by coupling together the outer edge of the inner layer of the first side wall with the outer edge of the inner layer of the second side wall to form an interior for storing at least one alcohol-sensitive pad. The alcohol-sensitive pads are placed between the first and second side wall before they are coupled together in a vacuum environment so that no air remains in the interior of the package.

At least one alcohol-sensitive pad is provided within the interior of the package. The alcohol-sensitive pad comprises a piece of paper saturated with alcohol oxidase enzyme, alcohol peroxidase enzyme, dyes and a buffer. The alcohol-sensitive pads are preferably cut into small pieces less than one-half square inch in size. The alcohol-sensitive pads are attached to the end of a stick so that the user may place the alcohol-sensitive pad within his mouth to saturate the pad with saliva or may dip the alcohol-sensitive pad into saliva that has been collected in a cup.

In a further preferred embodiment of the present invention, the instructions for use and the range of colors of the alcohol-sensitive pad and their corresponding blood alcohol levels are printed on the lower surface of the bottom layer of the second side wall. The range of colors may be printed either by showing each specific color together with its specific blood alcohol level or by showing the continuum of colors together with blood alcohol levels printed along the continuum. Thus, by printing the instructions for use and range of colors on the exterior of the package, a self-contained personal blood alcohol level testing kit is provided.

Preferably, the user performs the personal blood alcohol level test after abstaining from eating or drinking for at least fifteen minutes prior to taking the test. The test is administered by saturating the alcohol-sensitive pad at the end of the stick with the user's saliva. Once the pad is completely saturated, the user waits approximately two minutes for the alcohol-sensitive pad to change color. The user then compares the color of the alcohol-sensitive pad with the range of colors that are preferably printed on the bottom layer of the second side wall along with their corresponding blood alcohol levels. The user then matches the color of the alcohol-sensitive pad with the color printed on the second side wall and reads the corresponding blood alcohol level. Thus, an easy-to-administer test is provided that is accurate and reproducible and does not require the taking of blood.

In a further preferred embodiment of the present invention, the first and second side walls are rectangularly shaped. The first and second side walls are preferably made of a size that will fit in the user's wallet, approximately three and a half inches long by two inches wide. The top layer of the first side wall and the bottom layer of the second side wall, being preferably formed from paper, provides a package that may be opened by the user by tearing the first and second side walls to reveal the alcohol-sensitive pads stored in the interior of the package.

In a further preferred embodiment of the present invention, the first side wall comprises a plastic covering layer coupled together with the upper surface of the outer layer of the first side wall. The plastic covering layer is substantially rigid to protect the alcohol-sensitive pads contained within the package from any bending that may occur while the package is stored in a wallet, pocket or purse of the user.

By providing a package for the alcohol-sensitive pads that has high grade surgical aluminum foil as the inner layer of the first side wall and inner layer of the second side wall, the alcohol-sensitive pads may be stored in the interior of the package without being exposed to ultraviolet light, moisture or air. Further, more than one alcohol-sensitive pad may be stored within this package so that the test may be performed more than once in an evening or by more than one person. The size of this package can be small enough to be portable and be discreetly carried in a wallet, pocket or purse without damage to the alcohol-sensitive pads by use of the substantially rigid plastic covering layer coupled together to the outer layer of the first side wall. Further, the package, being constructed of aluminum foil, paper and plastic, is manufactured from inexpensive materials that is also inexpensive to manufacture. By providing the instructions for use and the range of colors of the alcohol-sensitive pad and their corresponding blood alcohol levels on the bottom layer of the second side wall, the personal blood alcohol level testing kit is self-contained and is easy to administer.

Other objects, features and advantages of the invention will become apparent from a consideration of the following detailed description and from the accompanying drawings.

DETAILED DESCRIPTION OF THE PREFERRED EMBODIMENT

The present invention is embodied in a package for storing the alcohol-sensitive pads of a personal blood alcohol level testing kit that is capable of storing the alcohol-sensitive pads without exposing them to ultraviolet light, moisture or air, which is portable so that it may be discreetly carried in a wallet, pocket or purse, which is inexpensive, which is easy to administer, which is accurate and reproducible and which is self-contained.

Figure 1:
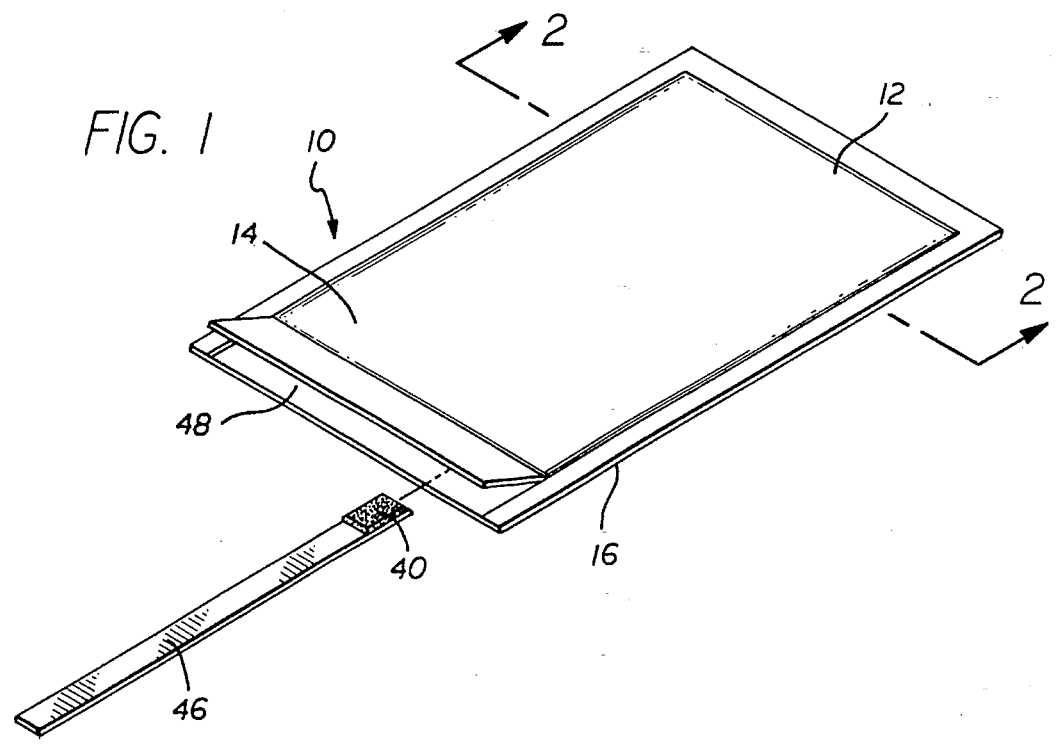
FIG. 1 is a top plan view of the package for storing the alcohol-sensitive pads of a personal blood alcohol level testing kit showing one of the alcohol-sensitive pads and sticks with which one embodiment of the present invention can be used.

In the particular embodiment shown in the drawings and herein described, the personal blood alcohol level testing kit 10 (see FIGS. 1 and 2) is particularly suited for storing the alcohol-sensitive pads of the testing kit without exposing them to ultraviolet light, moisture or air. The package 12 comprises a first side wall 14 and a second side wall 16. Both the first and second side walls (14 and 16, respectively) comprise an inner and outer layer, (18 and 20, respectively, for the first side wall and 22 and 24, respectively, for the second side wall). The inner layer 18 of the first side wall 14 and the inner layer 22 of the second side wall 16 is formed from aluminum foil. The aluminum foil used is preferably a high grade surgical aluminum foil. It has been found that the high grade surgical aluminum foil is preferred over other types of aluminum foils because this type of aluminum foil does not give off any oils that could damage the alcohol-sensitive pads during prolonged storage times. The outer layer 20 of the first side wall 14 and the outer layer 24 of the second side wall 16 are preferably formed from paper. By providing a first and second side wall that are formed from paper and aluminum, the first and second side walls of the package are easily opened by tearing by the user.

Figure 2:
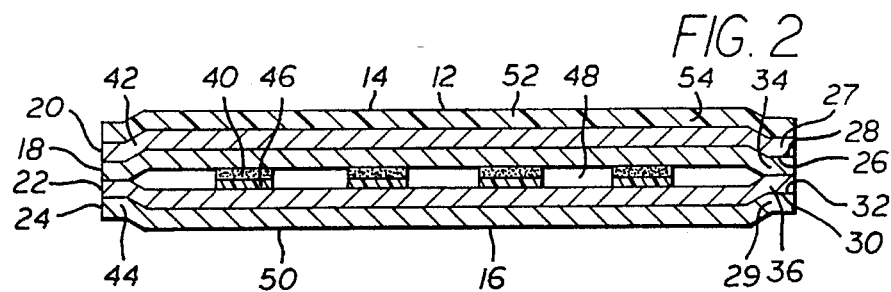
FIG. 2 is a side cross-sectional view taken along the line 2—2 in FIG. 1 containing four sticks with pads.

As shown in FIG. 2, the first side wall 14 is formed by coupling together the lower surface 26 of the outer layer 20 of the first side wall 14 with the upper surface 28 of the inner layer 18 of the first side wall 14. When coupled together, the outer edge 27 of the outer layer 20 is preferably contiguous with the outer edge 34 of the inner layer 18. Any type of adhesive material that is well-known in the art for coupling aluminum foil to paper may be used for coupling together these two layers. The second side wall 16 is formed by coupling together the lower surface 30 of the inner layer 22 of the second side wall 16 with the upper surface 32 of the outer layer 24 of the second side wall 16. When coupled together, the outer edge 36 of inner layer 22 is preferably contiguous with the outer edge 29 of the outer layer 24. Again, any adhesive well-known in the art may be used for coupling these layers together.

The package 12 for storing the alcohol-sensitive pads of a personal blood alcohol level testing kit of the present invention is then preferably formed by coupling together the outer edge 34 of the inner layer 18 of the first side wall 14 with the outer edge 36 of the inner layer 22 of the second side wall 16 to form an interior 48 for storing at least one alcohol-sensitive pad 40. (See FIG. 2). The inner layer 18 of the first side wall 14 and the inner layer 22 of the second side wall 16, which are both preferably formed from high grade surgical aluminum, are facing each other and form the inside lining of the interior 48 of the package 12.

When the first side wall 14 and the second side wall 16 are coupled together, the alcohol-sensitive pads 40, which are attached to sticks 46, are placed between the two side walls in a vacuum environment so that the alcohol-sensitive pads do not contact any air when they are placed into the package 12 or when they are stored in the interior 48 of the package 12. Thus, the alcohol-sensitive pads of the testing kit are maintained within an environment in which their only contact is with the inner layer 18 of the first side wall 14 and the inner layer 22 of the second side wall 16, both formed from the high grade surgical aluminum foil. The exterior of the package 12 that is exposed to ultraviolet light, moisture and air, are the outer layer 20 of the first side wall 14 and the outer layer 20 of the second side wall 16, which are formed from paper. The package, having the high grade surgical aluminum foil interior and paper exterior is able to store the alcohol-sensitive pads of the testing kit in its interior 48 without exposing the alcohol-sensitive pads to any ultraviolet light, moisture or air.

At least one alcohol-sensitive pad 40 is preferably provided within the interior 48 of the package 12. The alcohol-sensitive pads 40 are preferably formed from a piece of paper saturated with alcohol oxidase enzyme, alcohol peroxidase enzyme, dyes and a buffer. The alcohol-sensitive pads that are preferred are the Alco Screen™ pads manufactured by Chramatics, Inc. of Indianapolis, Ind. The alcohol-sensitive pads 40 are cut into small pieces and are rectangularly shaped, preferably being one quarter inch long by three-eighths inches wide. The alcohol-sensitive pads 40 are preferably mounted by any adhesive well-known in the art to one end of a thin plastic stick 46. Any type of plastic that can be formed into thin flexible sticks that is well-known in the art may be used to form stick 46. The stick 46 is preferably as wide as the alcohol-sensitive pad 40 and long enough so that the user can place the alcohol-sensitive pad within his mouth without placing the user's hand into the user's mouth.

Figure 3:
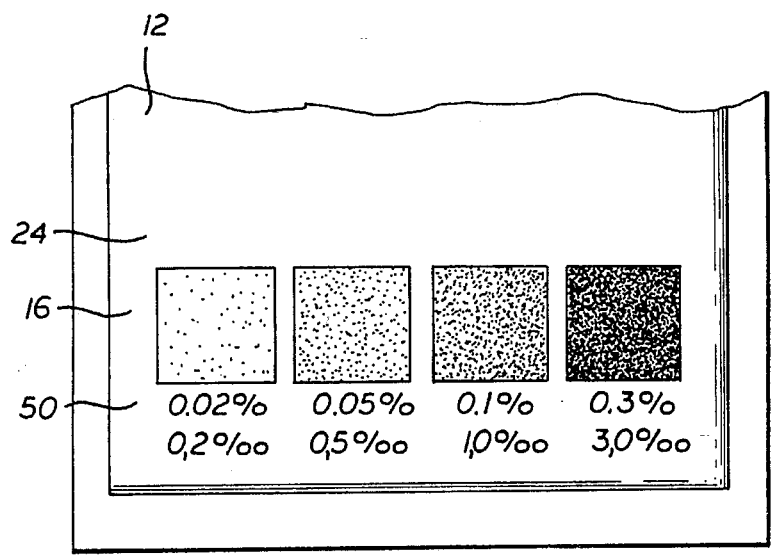
FIG. 3 is a top elevational view of the exterior of the package showing the instructions for use and range of colors and their corresponding blood alcohol levels printed thereon.

The Alco Screen™ pads are designed to change colors along a continuum. Thus, as the blood alcohol level of the user increases, then the color of the alcohol-sensitive pad becomes darker. In one preferred embodiment of the present invention, the ranges of colors to which the alcohol-sensitive pads may change are printed on the exterior of the package 12 on either the lower surface 50 of the bottom layer 24 of the second side wall 16 or the upper surface 52 of the top layer 18 of the first side wall 14. (See FIG. 3). The range of colors may be printed showing a plurality of specific colors along with their corresponding blood alcohol levels as shown in FIG. 3 or may be printed showing the continuum of color changes along with the continuum of corresponding blood alcohol levels (Not shown in FIG. 3.) The range of colors and corresponding blood alcohol levels that are preferably printed on the exterior of the package 12 are shown in FIG. 3 as 0.02, 0.05, 0.1 and 0.3% by volume blood alcohol levels. Other alcohol-sensitive pads having more noticeable color changes at different blood alcohol levels than those of the Alco Screen™ pad may be chosen. For instance, an alcohol-sensitive pad that noticeably changes colors at blood alcohol levels of 0.04% and 0.08% by volume blood alcohol levels may be desirable because Federal law sets the limit for drunk driving at 0.04% by volume blood alcohol and most states set the limit for drunk driving at 0.08% by volume blood alcohol. Thus, noticeable color changes at these alcohol levels will easily inform the user when they are at a blood alcohol level considered by either Federal or state law to be a drunk driver.

The instructions for administering the blood alcohol level test may also be printed on the exterior of the package 12 along with the colors as described above. By printing the instructions and the range of colors of the alcohol-sensitive pads either individually or on a continuum as discussed above, along with their corresponding blood alcohol levels, a self-contained personal blood test is provided, that is, the entire test is contained within and on the packaging.

The user preferably performs the blood alcohol test as follows. First, the user should abstain from eating or drinking for at least 15 minutes prior to taking the test. The user then opens the package 12 by tearing open the first and second side walls, 14 and 16, respectively, to reveal the alcohol-sensitive pads 40 and sticks 46 within the interior

48. The user then preferably saturates the alcohol-sensitive pads 40 with the user's saliva, preferably by either placing the alcohol-sensitive pad end of the stick 46 into the mouth and saturating the alcohol-sensitive pad 40 with saliva. The user may also place their saliva in a cup and saturate the alcohol-sensitive pad 40 in the saliva. The user then preferably waits approximately two minutes for the alcohol-sensitive pad 40 to change color. The user then compares the color of the alcohol-sensitive pad 40 with the range of colors that are preferably printed on the exterior of the package 12, along with their corresponding blood alcohol levels. The user then matches the color of the alcohol-sensitive pad with the color printed on the second side wall and reads the corresponding blood alcohol level. Thus, as can be seen, the test is easy to administer and does not require the taking of blood by the user. Further, it can be seen that the test is self-contained and requires no other outside parts other than the user's saliva to perform.

In a further preferred embodiment of the present invention, the first and second side walls 14 and 16 respectively, are rectangularly shaped. It is preferable that the package containing the personal blood alcohol level testing kit be portable so that it can be discreetly carried in a wallet, pocket or purse. Thus, one preferred size for making the first and second side walls is a size approximating that of a business card, which are commonly held within a wallet. This size is preferably rectangular, being three and a half inches long by two inches wide.

In a further preferred embodiment of the present invention, the first side wall 14 further comprises a plastic covering layer 52 coupled together with the upper surface 54 of the outer layer 20 of the first side wall 14. (See FIG. 2). The plastic covering layer 52 may also be coupled to the lower surface 50 of the outer layer 24 of the second side wall 16 (Not shown in FIG. 2). The plastic covering layer 52 is substantially rigid to protect the alcohol-sensitive pads 40 and sticks 46 contained within the package 12 from any bending that may occur while the package is stored within a wallet, pocket or purse of the user. Further, the plastic covering layer 52 may be imprinted with the logo of a company who may provide the user with a complimentary personal blood alcohol level testing kit 10, both as an advertisement and as a public service to prevent drunk driving. The plastic covering layer is preferably formed from any plastic that can be formed into thin, substantially rigid sheets that can be imprinted with color printing.

While a particular form of the invention has been illustrated and described, it will be apparent that various modifications can be made without departing from the scope of the invention. For instance, the size and shape of the first and second side walls may be chosen as preferred by the manufacturer in any size and shape so long as the sticks and the alcohol-sensitive pads are contained within the interior of the package. Further, alcohol-sensitive pads may be chosen that noticeably change color at blood alcohol levels of 0.04% by volume and 0.08% by volume. Accordingly, it is not intended that the invention be limited by the specific embodiment disclosed in the drawings and described in detail hereinabove.

What is claimed is:

1. A personal blood alcohol level testing kit for testing the blood alcohol level of a user, comprising:
   at least one pad being chemically sensitive to alcohol; and
   a package having an interior being formed from high grade surgical aluminum foil, the pads being stored within the package.

2. The personal blood alcohol level testing kit of claim 1 further including at least one stick having an end wherein the pad is attached to the end of the stick and wherein the stick is stored within the package.

3. The personal blood alcohol level testing kit of claim 1 wherein the exterior of the package is formed from paper.

4. The personal blood alcohol level testing kit of claim 1 wherein the pad is formed from paper and is impregnated with at least one alcohol-sensitive enzyme, at least one dye and at least one buffer, wherein when the alcohol sensitive enzyme comes in contact with the user's saliva, the dye changes colors only at predetermined blood alcohol levels of the user.

5. The personal blood alcohol level testing kit of claim 1 wherein the package has an exterior having the range of colors of the pads and their corresponding blood alcohol levels printed thereon.

6. The personal blood alcohol level testing kit of claim 1 wherein the package has an exterior having the instructions for use of the blood alcohol level testing kit printed thereon.

7. The personal blood alcohol level testing kit of claim 1 wherein the package has an enclosed interior, the enclosed interior containing substantially no air.

8. A personal blood alcohol level testing kit for testing the blood alcohol level of a user, comprising:
   at least one pad being chemically sensitive to alcohol, the pad being formed from paper and being impregnated with at least one alcohol-sensitive enzyme, at least one dye and at least one buffer, wherein when the alcohol sensitive enzyme comes in contact with the user's saliva, the dye changes colors only at predetermined blood alcohol levels of the user; and
   a package for storing the pad, the package being formed from paper and high grade surgical aluminum foil.

9. The personal blood alcohol level testing kit of claim 8 wherein the package includes:
   a first side wall having an outer edge and being comprised of a plurality of layers coupled together, at least one of the layers being formed from aluminum foil; and
   a second side wall having an outer edge and being comprised of a plurality of layers coupled together, at least one layer being formed from aluminum foil,
   wherein the outer edge of the first side wall is coupled together with the outer edge of the second side wall to form an interior for storing at least one alcohol-sensitive pad.

10. The personal blood alcohol level testing kit of claim 8 further including at least one stick having an end wherein the alcohol-sensitive pad is attached to the end of the stick and wherein the stick is stored within the interior of the package.

11. The personal blood alcohol level testing kit of claim 9 wherein one of the layers of the first side wall is a substantially rigid plastic layer.

12. The personal blood alcohol level testing kit of claim 9 wherein one of the layers of the first side wall is printed with the range of colors of the pads and their corresponding blood alcohol levels.

13. The personal blood alcohol level testing kit of claim 9 wherein one of the layers of the first side wall is printed with the instructions for use of the blood alcohol level testing kit.

14. The personal blood alcohol level testing kit of claim 9 wherein the first side wall and second side wall are rectangular.

15. The personal blood alcohol level testing kit of claim 9 wherein at least one of the layers of the first side wall and at least one of the layers of the second side wall are formed from paper.

16. The personal blood alcohol level testing kit of claim 9 wherein the aluminum foil layer of the first side wall and the aluminum foil layer of the second side wall is formed from high grade surgical aluminum foil.

17. The personal blood alcohol level testing kit of claim 9 wherein the interior of the package contains substantially no air.

18. A method for determining the blood alcohol level of a user, comprising:

opening a package formed from high grade surgical aluminum foil and containing at least one pad being chemically sensitive to alcohol;

saturating one of the pads with the user's saliva;

waiting approximately two minutes for the pad to change color;

comparing the color of the pad with the range of colors and corresponding blood alcohol levels printed on the exterior of the package; and matching the color of the alcohol sensitive pad to the corresponding color printed on the exterior of the package to determine the user's blood alcohol level.

* * * * *